(12) United States Patent
Marion et al.

(10) Patent No.: US 6,191,325 B1
(45) Date of Patent: Feb. 20, 2001

(54) RECOVERING/RECYCLING NITRIC ACID FROM DINITRATION PROCESS STREAMS COMPRISING $HNO_3$/DINITRO COMPOUNDS

(75) Inventors: Philippe Marion, Vernaison; Pascal Metivier, Sainte Roy le Lyon, both of (FR)

(73) Assignee: Rhodia Chimie, Courbevoie Cedex (FR)

( * ) Notice: Under 35 U.S.C. 154(b), the term of this patent shall be extended for 0 days.

(21) Appl. No.: 09/130,348

(22) Filed: Aug. 13, 1998

(30) Foreign Application Priority Data

Aug. 13, 1997 (FR) .................................................. 97-10347

(51) Int. Cl.$^7$ ................................................. C07C 205/00
(52) U.S. Cl. ........................................... 568/932; 568/930
(58) Field of Search ...................... 568/932, 930

(56) References Cited

U.S. PATENT DOCUMENTS 4,261,908 * 4/1981 Schroeder et al. ................... 568/932
5,006,325 * 4/1991 Parks et al. .......................... 568/932
5,345,012 * 9/1994 Schieb et al. ........................ 568/934

* cited by examiner

Primary Examiner—Shailendra Kumar
Assistant Examiner—J. Parsa
(74) Attorney, Agent, or Firm—Burns, Doane, Swecker & Mathis, L.L.P.

(57) ABSTRACT

Dinitro aromatic compounds are improvedly prepared by reacting an aromatic compound with a nitric acid nitrating agent and thence separating the nitrating acid from the process stream thus formed, the process stream containing said at least one dinitro aromatic compound and also having a fraction of the nitrating acid dissolved therein, the subject process also comprising (a) distilling/stripping nitric acid from said process stream, (b) recovering nitric acid from the top of the distillation/stripping vessel and recycling same to the nitration reaction and (c) washing the process stream which contains the at least one dinitro aromatic compound, but having the nitric acid removed therefrom.

20 Claims, No Drawings

RECOVERING/RECYCLING NITRIC ACID FROM DINITRATION PROCESS STREAMS COMPRISING HNO$_3$/DINITRO COMPOUNDS

CROSS REFERENCE TO PRIORITY APPLICATION

This application claims priority under 35 U.S.C. §119 of FR-97/10347, filed Aug. 13, 1997, assigned to the assignee hereof and hereby expressly incorporated by reference.

BACKGROUND OF THE INVENTION

1. Technical Field of the Invention

The present invention relates to the recovery of nitric acid contained in a process stream comprising dinitrated aromatic compounds, and more especially, relates to the recovery and recycling of nitric acid contained in an organic stream principally comprising dinitrated aromatic compounds.

2. Description of the Prior Art

Processes for preparing aromatic dinitrated compounds have long been carried out on an industrial scale. These compounds are valuable intermediates for the preparation of aromatic diamines which themselves are used for synthesizing the corresponding isocyanates. The isocyanates are advantageously converted into polyurethanes, the applications of which are very extensive.

In brief, dinitration reactions are typically carried out in two steps, the first entailing preparing the mononitrated compounds and the second preparing the dinitro compounds. Other than the aromatic compound reactant, a nitrating acid is employed which is generally a nitric acid/sulfuric acid mixture, the sulfuric acid being a catalyst for the reaction.

After each nitration step, the dinitrated compound is separated from the residual acid. This operation conventionally is carried out by direct settling of the reaction mixture or by centrifuging the latter.

Apart from the mononitrated compounds used for synthesizing the desired dinitrated compounds, the dinitrated compounds obtained after separation together with the nitrating acid (also deemed "crude dinitrated compounds") cannot be used as such since they always contain, in the dissolved state, a fraction of the nitrating acid as well as organic impurities.

Solving the problems associated with the purification of aromatic dinitrated compounds, and more particularly with the separation and recovery of the dissolved acid, has been the subject of considerable research.

This is because, given the tonnage of dinitrated compounds produced annually, it is a not insignificant economic advantage to recover these residual acids. Moreover, their recovery also impacts the environment since such recovery has, in particular, the consequence of limiting aqueous discharge. In addition, recovering the acids makes it possible to reduce the necessary cost of treating waste water, which cannot be discharged as is since it is contaminated with salts, such as sulfates and, more significantly, nitrates.

The known technique for separating and recovering the dissolved nitric acid have all focused on increasing the effectiveness with which the dinitrated compounds are washed.

In the alternative described in EP-279,312, crude dinitrotoluene is washed with a very small amount of water. In this fashion, the wash water, laden with nitric and sulfuric acids, is sufficiently concentrated to be directly recycled into the nitration process. However, such a process presents the drawback of requiring a special apparatus for separating the aqueous phase from the organic phase, in this instance a coalescer. This is because settling is difficult due to the very low water content used for the washing. Furthermore, the extraction efficiencies are at most 72%.

The embodiment described in EP-736,514 entails washing, in several countercurrent steps, the crude dinitrotoluene with water laden with acids which are employed in the nitration reaction. The recovered water may be recycled into the nitration process, without prior concentration, or, preferably, with prior concentration. However, this process does not have all of the desired safety guarantees, since the step of concentrating the acidulated water, which proves to be necessary in most cases, presents not insubstantial risks. This because the distilled aqueous phase comprises both the nitrating acid and the dissolved dinitrotoluene. Consequently, the conditions are for the nitration of a dinitrotoluene, resulting in trinitrotoluene, the dangerous properties of which are well known to this art. Moreover, the dinitrotoluene and its isomers present in the aqueous acid phase emanating from the wash operation are not recovered in cases in which the concentration of said water is carried out. This because such compounds are entrained with the water during distillation, and are lost. Too, the dinitrated compounds may cause the concentration column to become blocked or fouled, since they condense at the top of the column and are then in a solid form. Likewise, they may be present in the water intended to be discharged, causing pollution or added cost if it is necessary to remove them. Finally, in order to have good nitric and sulfuric acid recovery efficiencies, it is necessary to employ two or three washing stages, in other words at least two or three mixer/settler units comprising, for each of the units, a step of recycling the aqueous phase. Consequently, the process is complex to implement and requires a significant amount of investment.

SUMMARY OF THE INVENTION

According, a major object of the present invention is the provision of an improved, simpler technique for recovering nitric acid from dinitration process streams comprised thereof.

Briefly, the present invention features treating a process stream obtained via (1) the dinitration of aromatic compounds with a nitrating acid comprising at least nitric acid and then (2) separating the nitrating acid, such process stream comprising an aromatic dinitrated compound in which a fraction of the nitrating acid remains dissolved.

The process according to the invention thus comprises (a) distilling or stripping the aforementioned process stream;

(b) recovering nitric acid at the top of the step (a) distillation/stripping column and recycling same back to the nitration reaction vessel; and (c) washing the process stream freed of the nitric acid and comprising, inter alia, the dinitrated aromatic compounds.

DETAILED DESCRIPTION OF BEST MODE AND SPECIFIC/PREFERRED EMBODIMENTS OF THE INVENTION

More particularly according to the present invention, it has now unexpectedly and surprisingly been found that distilling the dinitrated aromatic compounds did not promote degradation thereof, for example, by reaction of said nitrated compounds with the nitrating acid present in the process stream, which could have formed dangerous compounds and presented difficulties in implementing the process, from a safety standpoint.

It should be appreciated that no process described in the prior art suggests carrying out such a distillation treatment directly on a process stream principally comprising dinitrated aromatic compounds. This because distillations of this type are conventionally carried out on aqueous effluents comprising only minimal amounts of nitrated organic compounds, as is apparent, e.g., from European Patent Application EP-736,514.

To the contrary, the subject process is much more desirable from a safety standpoint since, because the residence time in which distillation is carried out is minimal, the overall amount of nitrated aromatic compounds in the installation is considerably reduced, which represents a very major advantage. This characteristic has not been achieved in the case of the conventional processes for washing crude nitrated aromatic compounds.

Furthermore, the process according to the invention makes it possible, if not advantageously to replace the water-washing steps conventionally employed, to in any event limit the number of steps required for attaining good separation.

Too, the nitric acid recovery efficiency is very good, permitting recovery of at least 95% or even all of the nitric acid contained in the process stream of aromatic dinitrated compounds.

This result has a direct effect on the quality of the aqueous effluents emanating from the subsequent steps of washing the aromatic nitrated compounds which still comprise sulfuric acid and organic byproducts. This because such effluents have considerably reduced nitrate contents, thereby simplifying the steps of treating the wastewater before it is discharged.

Finally, the process according to the invention permits recovering nitrous vapors.

As indicated above, the present invention features the separation and recovery of nitric acid contained in a process stream based on a nitrated aromatic compound.

By "nitrated aromatic compound" is intended a compound produced via dinitration of an aromatic starting substrate. It should be appreciated that hereinafter reference will be indiscriminately made to "dinitrated compounds" and to "nitrated compounds."

Aromatic compounds suitable for dinitration may comprise one or more aromatic ring members. Representative thereof are benzene and derivatives thereof, naphthalene and derivatives thereof, phenanthrene and derivatives thereof, biphenyl, diphenyl oxide and derivatives thereof, etc.

By "derivatives" are intended aromatic radicals containing one or more substituents such as $C_1$–$C_6$ alkyl or $C_3$–$C_6$ cycloalkyl radicals; hydroxyl radicals; $C_1$–$C_6$ alkoxy radicals; $C_1$–$C_4$ aminoacylated radicals; halogen atoms, and the like.

Exemplary alkyl or cycloalkyl radicals include methyl, ethyl, n-propyl, isopropyl, n-butyl, isobutyl, tert-butyl, n-hexyl and cyclohexyl radicals.

Exemplary alkoxy radicals include methoxy, ethoxy and propoxy radicals.

And exemplary aminoacylated radicals include acetylamine and benzoylamine radicals, in particular.

Any halogen is suitable, whether fluorine, chlorine, bromine or iodine.

Preferably, the aromatic starting compound for nitration reactions is selected from among benzene, toluene, xylene and isomers thereof, ethylbenzene, propylbenzene, isopropylbenzene, chlorobenzene, chloromethylbenzene and isomers thereof, chloroethylbenzene and isomers thereof, biphenyl, diphenyl oxide, etc.

In one particular embodiment of the invention, the process stream treated emanates from the dinitration of benzene, or preferably of toluene.

The process stream comprising the dinitrated aromatic compound is therefore provided by carrying out a nitration reaction on the corresponding aromatic compound, in the presence of a sulfuric/nitric nitrating acid. Thus, the nitrating acid more particularly comprises a mixture of nitric acid and of sulfuric acid. Next, the dinitrated aromatic compounds are then separated from the residual nitrating acid to provide the process stream which will be treated in accordance with the process according to the invention.

Advantageously, this operation is carried out by simple settling or centrifuging of the reaction mixture.

The dinitrated aromatic compounds thus freed (or stripped) of the major fraction of the nitrating acid are conventionally designated "crude aromatic dinitrated compounds."

According to the first step of the process according to the invention, an operation of distilling or stripping the process stream comprising the dinitrated aromatic compound is carried out.

As indicated above, the treated process stream corresponds to the crude dinitrated compounds.

More particularly, the stream treated in accordance with the invention has a dinitrated aromatic compound content of at least 80% with respect to the total weight of the process stream, and, more advantageously, at least 90% with respect thereto.

For the purpose of indication, said stream typically has a nitric acid content of less than 10% by weight with respect to the total weight of the process stream and of any nitrous vapor. Preferably, the nitric acid content in the stream to be treated is less than 5% by weight with respect to the same reference.

The treated process stream may furthermore comprise sulfuric acid.

In a first embodiment, the sulfuric acid content is less than 3% by weight with respect to the aromatic dinitrated compounds. This sulfuric acid content is conventional for reaction mixtures emanating from nitration reactions by means of a sulfuric/nitric mixture.

In a second embodiment, the sulfuric acid content is such that, after the nitric acid has been extracted in accordance with step (a) of the process of the invention, the process stream comprising the nitrated compounds settles. Generally, said content is greater than approximately 3% by weight with respect to the weight of the dinitrated compounds. In this embodiment, it is clearly advantageous to recycle the sulfuric acid employed. For example, it may be added to the residual acid stream of the nitration process in order, optionally, to be concentrated. Subsequently, this process stream is again introduced into the nitration process.

Finally, the process stream to be treated may comprise water. This content can vary and depends on the sulfuric acid content. For example, and in the event the sulfuric acid content is low, the water content is less than 0.3% with respect to the weight of the aromatic dinitrated compounds.

The operation is typically carried out to separate the amount of nitric acid present. Generally, this amount is equivalent to at most 10% by weight with respect to the weight of aromatic dinitrated compounds. Preferably, this amount corresponds to 1% to 5% by weight with respect to the same reference.

Step (a) is carried out more particularly in a column comprising 1 to 4 theoretical plates.

More advantageously, step (a) is carried out in a column comprising only one theoretical (flash) stage.

In a second embodiment, step (a) is carried out in a film evaporator.

Step (a) may furthermore be carried out with or without stirring. Preferably, the separation operation is carried out without stirring.

One preferred embodiment of the subject process entails conducting the separation step (a) under a pressure of from $10^3$ Pa to atmospheric pressure (approximately $10^5$ Pa).

In another preferred embodiment, a vacuum distillation is carried out. More particularly, this separation is carried out under a pressure of from $10^3$ to $10^4$ Pa.

In a second such embodiment, a stripping operation, i.e., a separation by entrainment of the nitric acid with a carrier gas, is carried out.

According to this embodiment, the pressure is approximately atmospheric pressure.

Furthermore, the carrier gas is advantageously and preferably nitrogen. Rare gases, such as helium or argon, are also suitable for carrying out this step. Preferably, the carrier gas is dry.

It will be appreciated that even in the context of a vacuum distillation operation, it is preferable to maintain a controlled, dry and inert atmosphere in the apparatus.

Step (a) is carried out at a temperature greater than the melting point of the nitrated compounds present in the process stream. However, the temperature is less than the degradation temperature of the components of the treated stream, i.e., essentially of the aromatic nitrated compounds. Of course, this temperature not only depends on the operating conditions for separating the aromatic nitrated compounds, but also depends on the fact that it is desired to separate the nitric acid without entraining the aromatic nitrated compounds.

In the particular case of dinitrotoluene and isomers thereof, this temperature is less than approximately 130° C. If the separation is carried out under the reduced-pressure conditions indicated above, the temperature at which the distillation is performed in step (a) ranges from 50° to 100° C. More preferably, the temperature ranges from 60° to 80° C.

The stream recovered at the top of the distillation or stripping plant, and comprising nitric acid, may advantageously be recycled.

Thus, a first embodiment of step (b) of the process according to the invention entails recycling the stream recovered at the top of the distillation or stripping plant (column), and comprising nitric acid, back into the nitration process.

For example, the stream at the top of the distillation or stripping apparatus may be recycled directly into any point in the nitration sequence.

It should be appreciated that for a dinitration operation, carried out in two steps, it does not matter whether the stream is recycled into the mononitration reaction or into the dinitration reaction. Preferably, the stream under consideration is returned to the mononitration reaction.

Likewise, it may be absorbed, without prior condensation, in sulfuric acid and/or water before being recycled into the nitration process.

Too, it is possible to treat this stream to recover any nitrous vapor, carrying out any conventional nitrous vapor recovery process such as, for example, any process of oxido-absorption under pressure.

Finally, step (c) of the process according to the invention entails treating the stream recovered at the base of the distillation or stripping vessel, which stream comprises the aromatic dinitrated compounds, the sulfuric acid and the organic byproducts, such as to separate the aromatic dinitrated compounds from the sulfuric acid and byproducts.

This operation conventionally is carried out by means of one or more washing steps.

If the amount of sulfuric acid present in the process stream emanating from step (a) is greater than approximately 3% with respect to the aromatic dinitrated compounds, step (c) is carried out after first separating the sulfuric acid present in this stream.

This may be carried out via any technique known to the art, such as settling or centrifuging.

Advantageously, the sulfuric acid thus separated may be recycled into the nitration process, as indicated previously.

Step (c) will now be more fully described.

Thus, in one particular embodiment of the invention, a first step of washing with water is carried out to remove most of the sulfuric acid present. The remaining sulfuric acid (dilute sulfuric acid) can advantageously be recycled into the process. For example, it may be reintroduced into the nitration process proper, preferably after having been subjected to a concentration step, by itself or in combination with another process stream such as, especially, the residual mononitration acid. Likewise, it may be recycled into the washing step itself (loop). These two embodiments may be combined.

Although this washing step is optional, it is nevertheless recommended in order to achieve a good level of profitability of the process.

In a second step, the stream of nitrated compounds is washed in the presence of an aqueous solution of an alkaline agent (basic washing). The purpose of such an operation is to convert the sulfuric acid and the byproducts, which are principally hydroxynitroaromatic compounds, into salts which are soluble in the aqueous phase.

This alkaline agent is advantageously selected from among alkali or alkaline earth metal hydroxides and carbonates.

Whether with regard to the optional first washing operation with water or with regard to the second operation in the presence of an alkaline agent, these operations may be carried out in one or more steps, preferably countercurrent steps, if the option involving multiple steps is selected.

Next, whatever the washing operation carried out, all that is required is to separate the organic phase comprising the nitrated compounds from the aqueous phase.

In respect of this basic washing process, see European Patent Application EP-662,454.

The technique described in the aforementioned '454 patent application is particularly advantageous in the sense that basic water laden with polluting salts may be destroyed directly upon exiting the washing circuit, without entailing high costs.

However, it is possible to treat this aqueous effluent with oxidizing agents, which destroy the organic byproducts, before the water is discharged. Exemplary such oxidizing agents include sodium hypochloride and hydrogen peroxide. The use of such agents has been described, for example, in European Patent Application EP-654,463. However, other treatments may also be employed.

The aromatic nitrated compounds which have undergone the basic washing step may then be washed again, but using water, to remove any trace amounts of the alkaline agent.

Here again, the operation may be carried out in one or more steps, preferably countercurrent steps, if this is a multi-step washing process.

After these various washing steps, the aromatic nitrated compounds, and more particularly the compounds emanating from the dinitration of toluene, are suitable for the preparation of the corresponding amines, especially by hydrogenation in the presence of a nickel-based catalyst.

In order to further illustrate the present invention and the advantages thereof, the following specific example is given, it being understood that same is intended only as illustrative and in nowise limitative.

EXAMPLE

A LUWA film evaporator (surface area: 1.6 dm$^2$) was charged at a rate of 550 ml/h with crude dinitrotoluene having the following composition:

(a) 2.35% nitric acid (weight/weight of dinitrotoluene);
(b) 0.3% sulfuric acid (weight/weight of dinitrotoluene);
(c) trace amounts of water;
(d) nitrous vapor;
(e) dinitrotoluene q.s. for 100%.

The separation was carried out under a pressure of 2×10$^3$ Pa (20 mbar) and the temperature of the double-walled vessel was maintained at 65° C.

97% of the nitric acid and all of the dissolved NO$_2$ were recovered in two passes (equivalent to a single pass over an evaporator area of 3.2 dm$^2$).

Analyses evidenced that there was no degradation of the dinitrotoluene into trinitrotoluene.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of at least one dinitro aromatic compound which comprises reacting an aromatic compound with a nitric acid nitrating agent, wherein said nitrating agent is a mixture of nitric acid and sulfuric acid, and thence separating the nitrating acid from the process stream thus formed, said process stream comprising said at least 80% by weight of one dinitro aromatic compound and having a fraction of said nitrating acid dissolved therein, said process also comprising (a) distilling/stripping nitric acid from said process stream, (b) recovering nitric acid from the top of the distillation/stripping vessel and recycling same to said nitration reaction and (c) washing the process stream comprising said at least one dinitro aromatic compound, but having said nitric acid removed therefrom.

2. The process as defined by claim 1, said step (a) being carried out under a pressure ranging from 10$^2$ Pa to atmospheric pressure.

3. The process as defined by claim 1, said distillation being carried out under a pressure ranging from 10$^3$ to 10$^4$ Pa.

4. The process as defined by claim 1, comprising (a) stripping a process stream at a pressure of about atmospheric, in the presence of a carrier gas.

5. The process as defined by claim 4, said carrier gas comprising nitrogen or a rare gas.

6. The process as defined by claim 1, comprising (a) distilling said process stream at a temperature greater than the melting point of the dinitrated aromatic compounds contained therein.

7. The process as defined by claim 1, said step (a) being carried out in a column comprising 1 to 4 theoretical plates.

8. The process as defined by claim 1, said step (a) being carried out in a film evaporator.

9. The process as defined by claim 1, said step (a) process stream comprising less than 3% by weight of sulfuric acid, relative to the weight of said dinitro aromatic compounds.

10. The process as defined by claim 1, said step (a) process stream comprising greater than about 3% by weight of sulfuric acid, relative to the weight of said dinitro aromatic compounds.

11. The process as defined by claim 1, comprising (b) directly recycling said recovered nitric acid into any point in said nitration reaction.

12. The process as defined by claim 11, comprising sorbing said nitric acid in sulfuric acid and/or water prior to the recycling thereof.

13. The process as defined by claim 1, comprising (b) recovering nitric acid vapor from the top of said distillation/stripping vessel.

14. The process as defined by claim 10, comprising separating said sulfuric acid from said process stream prior to the step (c) washing thereof.

15. The process as defined by claim 14, comprising concentrating the sulfuric acid thus separated and recycling same to said nitration reaction.

16. The process as defined by claim 1, said reactant aromatic compound comprising one or more aromatic nuclei optionally substituted by at least one substituent selected from among $C_1$–$C_6$ alkyl or $C_3$–$C_6$ cycloalkyl radicals, hydroxyl groups, $C_1$–$C_6$ alkoxy radicals, $C_1$–$C_4$ aminoacyl radicals, and halogen atoms.

17. The process as defined by claim 16, said reactant aromatic compound comprising benzene or toluene.

18. The process as defined by claim 1, comprising (c) washing said process stream with water.

19. The process as defined by claim 1, comprising (b) recovering at least 95% of the nitric acid from said process stream.

20. The process as defined by claim 1, comprising a mononitration/dinitration sequence.

* * * * *